United States Patent
Wiesner (10) Patent No.: US 9,205,235 B2
(45) Date of Patent: *Dec. 8, 2015

(54) CANISTER FOR WOUND THERAPY AND RELATED METHODS THEREFOR

(75) Inventor: Joel D. Wiesner, St. Peters, MO (US)

(73) Assignee: Smith & Nephew, Inc., Memphis, TN (US)

( * ) Notice: Subject to any disclaimer, the term of this patent is extended or adjusted under 35 U.S.C. 154(b) by 847 days.

This patent is subject to a terminal disclaimer.

(21) Appl. No.: 13/465,595

(22) Filed: May 7, 2012

(65) Prior Publication Data

US 2012/0265160 A1    Oct. 18, 2012

Related U.S. Application Data (63) Continuation of application No. 12/205,186, filed on Sep. 5, 2008, now Pat. No. 8,177,763.

(51) Int. Cl.
| | |
|---|---|
| *A61M 1/00* | (2006.01) |
| *A61M 27/00* | (2006.01) |
| *A61F 13/00* | (2006.01) |

(52) U.S. Cl.
CPC .............. *A61M 27/00* (2013.01); *A61M 1/0049* (2013.01); *A61M 1/0052* (2014.02);
(Continued)

(58) Field of Classification Search
CPC ............ A61M 1/0001; A61M 1/0052; A61M 1/0056; A61M 1/0049; A61M 5/7536; A61M 5/36; A61M 5/38; A61M 5/385; A61F 13/00068
See application file for complete search history.

(56) References Cited

U.S. PATENT DOCUMENTS

| | | |
|---|---|---|
| 3,367,332 A | 2/1968 | Groves |
| 3,486,504 A | 12/1969 | Austin, Jr. |

(Continued)

FOREIGN PATENT DOCUMENTS

| | | |
|---|---|---|
| DE | 41 11 122 | 4/1993 |
| DE | 295 04 378 | 10/1995 |

(Continued)

OTHER PUBLICATIONS

US 6,216,701, 4/2001, Heaton et al. (withdrawn).

(Continued)

*Primary Examiner* — Philip R Wiest
*Assistant Examiner* — Ariana Zimbouski
(74) *Attorney, Agent, or Firm* — Knobbe, Martens, Olson & Bear, LLP (57) ABSTRACT

A portable system for subatmospheric pressure therapy in connection with healing a surgical wound includes a wound dressing dimensioned for positioning relative to a wound bed and a collection canister in fluid communication with the wound dressing. The canister includes a first vacuum chamber for drawing a vacuum and a second fluid chamber for collecting fluids removed from the wound dressing under the vacuum. The canister further includes a hydrophobic membrane separating the first and second chambers. The hydrophobic membrane is dimensioned to span a major portion of the cross-sectional area of the canister. The hydrophobic membrane may be dimensioned to substantially span an internal dimension of the collection canister. The hydrophobic membrane may include one or more outwardly extending lobes. The hydrophobic membrane may be releasably mountable to the canister, and, may be supported within a divider separating the first vacuum chamber and the second fluid chamber.

16 Claims, 5 Drawing Sheets

(52) U.S. Cl.
CPC .... *A61F 2013/00536* (2013.01); *A61M 1/0088* (2013.01); *A61M 2205/21* (2013.01); *A61M 2205/7536* (2013.01); *Y10T 29/494* (2015.01)

(56) References Cited

U.S. PATENT DOCUMENTS

| | | | |
|---|---|---|---|
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,266,545 A | 5/1981 | Moss | |
| 4,382,441 A | 5/1983 | Svedman | |
| 4,524,064 A | 6/1985 | Nambu | |
| 4,743,232 A | 5/1988 | Kruger | |
| 4,767,417 A | 8/1988 | Boehringer et al. | |
| 4,969,880 A | 11/1990 | Zamierowski | |
| 4,990,137 A | 2/1991 | Graham | |
| 4,997,438 A | 3/1991 | Nipper | |
| 5,071,409 A | 12/1991 | Rosenberg | |
| 5,100,395 A | 3/1992 | Rosenberg | |
| 5,100,396 A | 3/1992 | Zamierowski | |
| 5,106,629 A | 4/1992 | Cartmell et al. | |
| 5,141,503 A | 8/1992 | Sewell, Jr. | |
| 5,149,331 A | 9/1992 | Ferdman et al. | |
| 5,152,757 A | 10/1992 | Eriksson | |
| 5,160,322 A | 11/1992 | Scheremet et al. | |
| 5,176,663 A | 1/1993 | Svedman et al. | |
| 5,178,157 A | 1/1993 | Fanlo | |
| 5,195,977 A | 3/1993 | Pollitt | |
| 5,261,893 A | 11/1993 | Zamierowski | |
| 5,263,922 A | 11/1993 | Sova et al. | |
| D364,679 S | 11/1995 | Heaton et al. | |
| 5,484,427 A | 1/1996 | Gibbons | |
| 5,527,293 A | 6/1996 | Zamierowski | |
| 5,536,233 A | 7/1996 | Khouri | |
| 5,549,584 A | 8/1996 | Gross | |
| 5,588,958 A | 12/1996 | Cunningham et al. | |
| 5,636,643 A | 6/1997 | Argenta et al. | |
| 5,645,081 A | 7/1997 | Argenta et al. | |
| 5,678,564 A | 10/1997 | Lawrence et al. | |
| 5,701,917 A | 12/1997 | Khouri | |
| 5,733,305 A | 3/1998 | Fleischmann | |
| 5,840,049 A | 11/1998 | Tumey et al. | |
| 5,911,222 A | 6/1999 | Lawrence et al. | |
| 5,944,703 A | 8/1999 | Dixon et al. | |
| 6,010,524 A | 1/2000 | Fleischmann | |
| 6,071,267 A | 6/2000 | Zamierowski | |
| 6,099,493 A | 8/2000 | Swisher | |
| 6,117,111 A | 9/2000 | Fleischmann | |
| 6,135,116 A | 10/2000 | Vogel et al. | |
| D434,150 S | 11/2000 | Tumey et al. | |
| 6,142,982 A | 11/2000 | Hunt et al. | |
| 6,174,306 B1 | 1/2001 | Fleischmann | |
| 6,203,563 B1 | 3/2001 | Fernandez | |
| 6,261,276 B1 | 7/2001 | Reitsma | |
| 6,325,788 B1 | 12/2001 | McKay | |
| 6,345,623 B1 | 2/2002 | Heaton et al. | |
| 6,348,423 B1 | 2/2002 | Griffiths et al. | |
| 6,398,767 B1 | 6/2002 | Fleischmann | |
| 6,406,447 B1 | 6/2002 | Thrash et al. | |
| 6,420,662 B1 | 7/2002 | Ishikawa | |
| 6,458,109 B1 | 10/2002 | Henley et al. | |
| 6,488,643 B1 | 12/2002 | Tumey et al. | |
| 6,500,112 B1 | 12/2002 | Khouri | |
| D469,175 S | 1/2003 | Hall et al. | |
| D469,176 S | 1/2003 | Hall et al. | |
| 6,520,982 B1 | 2/2003 | Boynton et al. | |
| 6,547,255 B1 | 4/2003 | Donaway et al. | |
| 6,553,998 B2 | 4/2003 | Heaton et al. | |
| D475,134 S | 5/2003 | Randolph | |
| 6,557,704 B1 | 5/2003 | Randolph | |
| D478,659 S | 8/2003 | Hall et al. | |
| 6,607,495 B1 | 8/2003 | Skalak et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| D488,558 S | 4/2004 | Hall | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,887,228 B2 | 5/2005 | McKay | |
| 6,887,263 B2 | 5/2005 | Bleam et al. | |
| 6,936,037 B2 | 8/2005 | Bubb et al. | |
| 6,942,633 B2 | 9/2005 | Odland | |
| 6,942,634 B2 | 9/2005 | Odland | |
| 6,951,553 B2 | 10/2005 | Bubb et al. | |
| 6,960,181 B2 | 11/2005 | Stevens | |
| 6,979,324 B2 | 12/2005 | Byordi et al. | |
| 6,994,702 B1 | 2/2006 | Johnson | |
| 7,022,113 B2 | 4/2006 | Lockwood et al. | |
| 7,037,254 B2 | 5/2006 | O'Connor et al. | |
| 7,052,167 B2 | 5/2006 | Vanderschuit | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,719 B2 | 10/2006 | Rosenberg | |
| 7,128,735 B2 | 10/2006 | Weston | |
| 7,144,390 B1 | 12/2006 | Hannigan et al. | |
| 7,169,151 B1 | 1/2007 | Lytinas | |
| 7,182,758 B2 | 2/2007 | McCraw | |
| 7,195,624 B2 | 3/2007 | Lockwood et al. | |
| 7,198,046 B1 | 4/2007 | Argenta et al. | |
| 7,214,202 B1 | 5/2007 | Vogel et al. | |
| 7,216,651 B2 | 5/2007 | Argenta et al. | |
| D544,092 S | 6/2007 | Lewis | |
| 7,273,054 B2 | 9/2007 | Heaton et al. | |
| 7,276,051 B1 | 10/2007 | Henley et al. | |
| 7,279,612 B1 | 10/2007 | Heaton et al. | |
| 7,316,672 B1 | 1/2008 | Hunt et al. | |
| D565,177 S | 3/2008 | Locke et al. | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,396,345 B2 | 7/2008 | Knighton et al. | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,422,576 B2 | 9/2008 | Boynton et al. | |
| 7,438,705 B2 | 10/2008 | Karpowicz et al. | |
| 8,414,519 B2 * | 4/2013 | Hudspeth et al. | 604/10 |
| 2001/0031943 A1 | 10/2001 | Urie | |
| 2001/0043943 A1 | 11/2001 | Coffey | |
| 2002/0016577 A1 | 2/2002 | Ohmstede | |
| 2002/0143286 A1 | 10/2002 | Tumey | |
| 2002/0151836 A1 | 10/2002 | Burden | |
| 2003/0093041 A1 | 5/2003 | Risk, Jr. et al. | |
| 2003/0208149 A1 | 11/2003 | Coffey | |
| 2003/0212357 A1 | 11/2003 | Pace | |
| 2003/0212359 A1 | 11/2003 | Butler | |
| 2003/0219469 A1 | 11/2003 | Johnson et al. | |
| 2004/0006319 A1 | 1/2004 | Lina et al. | |
| 2004/0030304 A1 | 2/2004 | Hunt et al. | |
| 2004/0039415 A1 | 2/2004 | Zamierowski | |
| 2004/0064132 A1 | 4/2004 | Boehringer et al. | |
| 2004/0073151 A1 | 4/2004 | Weston | |
| 2004/0093026 A1 | 5/2004 | Weidenhagen et al. | |
| 2004/0122434 A1 | 6/2004 | Argenta et al. | |
| 2004/0193218 A1 | 9/2004 | Butler | |
| 2004/0241213 A1 | 12/2004 | Bray | |

(56) References Cited

U.S. PATENT DOCUMENTS

| | | | |
|---|---|---|---|
| 2004/0243073 | A1 | 12/2004 | Lockwood et al. |
| 2005/0010153 | A1 | 1/2005 | Lockwood et al. |
| 2005/0020955 | A1 | 1/2005 | Sanders et al. |
| 2005/0070835 | A1 | 3/2005 | Joshi |
| 2005/0070858 | A1 | 3/2005 | Lockwood et al. |
| 2005/0085795 | A1 | 4/2005 | Lockwood et al. |
| 2005/0177190 | A1 | 8/2005 | Zamierowski |
| 2005/0182445 | A1 | 8/2005 | Zamierowski |
| 2005/0222527 | A1 | 10/2005 | Miller et al. |
| 2005/0222544 | A1 | 10/2005 | Weston |
| 2005/0261642 | A1 | 11/2005 | Weston |
| 2005/0261643 | A1 | 11/2005 | Bybordi et al. |
| 2006/0015087 | A1 | 1/2006 | Risk, Jr. et al. |
| 2006/0025727 | A1 | 2/2006 | Boehringer et al. |
| 2006/0041247 | A1 | 2/2006 | Petrosenko et al. |
| 2006/0079852 | A1 | 4/2006 | Bubb et al. |
| 2006/0100586 | A1 | 5/2006 | Karpowicz et al. |
| 2006/0100594 | A1 | 5/2006 | Adams et al. |
| 2006/0116620 | A1 | 6/2006 | Oyaski |
| 2007/0014837 | A1 | 1/2007 | Johnson et al. |
| 2007/0021697 | A1 | 1/2007 | Ginther et al. |
| 2007/0027414 | A1 | 2/2007 | Hoffmann et al. |
| 2007/0032754 | A1 | 2/2007 | Walsh |
| 2007/0032755 | A1 | 2/2007 | Walsh |
| 2007/0032778 | A1 | 2/2007 | Heaton et al. |
| 2007/0055209 | A1 | 3/2007 | Patel et al. |
| 2007/0066946 | A1 | 3/2007 | Haggstrom et al. |
| 2007/0078366 | A1 | 4/2007 | Haggstrom et al. |
| 2007/0219513 | A1 | 9/2007 | Lina et al. |
| 2008/0011667 | A1 | 1/2008 | Ruschke |
| 2008/0082059 | A1 | 4/2008 | Fink et al. |

FOREIGN PATENT DOCUMENTS

| | | |
|---|---|---|
| DE | 43 06 478 | 12/2008 |
| EP | 0 020 662 | 7/1984 |
| EP | 0 358 302 | 3/1990 |
| EP | 0 853 950 | 10/2002 |
| GB | 1 549 756 | 3/1977 |
| GB | 2 195 255 | 4/1988 |
| GB | 2 235 877 | 3/1991 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 96/05873 | 2/1996 |
| WO | 9605873 | 2/1996 |
| WO | 03057307 | 7/2003 |
| WO | 03101508 | 12/2003 |
| WO | 2005009488 | 2/2005 |

OTHER PUBLICATIONS

US 7,186,244, 3/2007, Hunt et al. (withdrawn).
International Search Report Application No. PCT/US09/46890, dated Jul. 23, 2009.
Meyer, M.D., et al., "In Surgery, Medicine and the Specialties A Manual of its Practical Application", Bier's Hyperemic Treatment, Second Revised Edition, W.B. Saunders Company, 1909.
Jeter, Katherine F., et al., "Managing Draining Wounds and Fistulae: New and Established Methods", Chronic Wound Care, 1990, pp. 240-246.
Chariker, M. E. et al. (eds), "Effective Management of Incisional and Cutaneous Fistulae with Closed Suction Wound Drainage," Contemporary Surgery, vol. 34, Jun. 1989, pp. 59-63.
B.M. Kostiuchenok, et al., "The Vacuum Effect in the Surgical Treatment of Purulent Wounds," Russian Journal: Vestnik Khirurgii, Sep. 1986, (18-21).
Y.N. Usupov, et al., "Active Wound Drainage," Russian Journal: Vestnik Khirugii, Apr. 1987, (42-45).
Yu A. Davydov, et al., "Concepts for Clinical Biological Management of the Wound Process in the Treatment of Purulent Wounds Using Vacuum Therapy," Vestnik Khirugii, Feb. 1991, 132-135).
N.A. Bagautdinov (Kazan), "Variant of External Vacuum Aspiration in the Treatment of Purulent Diseases of Soft Tissues," UDC 616-002.36 (94-96), Date: 1986.
Chardack, et al., "Experimental studies on Synthetic Substitutes for Skin and Their Use in the Treatment of Burns," vol. 155, No. 1 (128-136), Date: 1961.
Gorica Zivadinovic, et al., "Vacuum Therapy in the Treatment of Peripheral Blood Vessels," Conference Papers of the 5th Timok Medical Days, Majdanpek, 1986 (161-164).
Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).
W. Fleischmann, et al., Vacuum Sealing: Indication, Technique and Results, Emr J Orthop Surg Tramatol (1995) 5:37-40.
Sherry Stoll, "Energetic Remedies—Cupping: Healing Within a Vacuum," https://www.suite101.com/article.cfm/energetic)remedies/74531, Apr. 13, 2005.
Mulder, G.D, et al., "Clinicians' Pocket Guide to Chronic Wound Repair," Wound Healing Publications Second Edition, 1991.
Yu A. Davydov, et al., "Vacuum Therapy in the Treatment of Purulent Lactation Mastitis," Russian Journal: Vesnik Khirurgii, Sep. 1986, (66-70).
Yu A. Davydov, et al., "Bacteriological and Cytological Assessment of Vacuum Therapy of Purulent Wounds", Vestnik Khirurgii, Oct. 1988, (48-52).
W. Fleischmann, "Vacuum Sealing for Treatment of Problematical Wounds", University Surgical Clinic and Polyclinic—Accident Surgery Department, WundForum Spezial—IHW 94, Date: 1994.
Goran Sanden, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Bjorn, et al., "Irrigation Treatment in Split-thickness Skin Grafting of Intractable Leg Ulcers," Scand J Plast Reconstr Surg 19: 211-213, 1985.
Paul Svedman, et al., "Staphylococcal Wound Infection in the Pig: Part I. Course," Annals of Plastic Surgery, vol. 23, No. 3, Sep. 1989 (212-218).
Paul Svedman, "A Dressing Allowing Continuous Treatment of a Biosurface," IRCS Medical Science: Biomedical Technology; Clinical Medicine; Surgery and Transplantation, 7, 221 (1979).
Paul Svedman, "Irrigation Treatment of Leg Ulcers," The Lancet, Sep. 3, 1983 (532-534).
H. Teder, et al., "Continuous Wound Irrigation in the Pig," Journal of Investigative Surgery, vol. 3 (399-407), Date: 1990.
P. Svedman, "A Dressing System Providing Fluid Supply and Suction Drainage Used for Continuous or Intermittent Irrigation," Annals of Plastic Surgery, vol. 17, No. 2, Aug. 1986 (125-133).
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

* cited by examiner

CANISTER FOR WOUND THERAPY AND RELATED METHODS THEREFOR

CROSS-REFERENCE TO RELATED APPLICATION

This application is a continuation application of and claims the benefit under 35 U.S.C. §120 to co-pending U.S. patent application Ser. No. 12/205,186, filed on Sep. 5, 2008, and titled CANISTER MEMBRANE FOR WOUND THERAPY, the entirety of which is hereby incorporated by reference for all purposes.

BACKGROUND

1. Technical Field

The present disclosure relates to treating an open wound, and, more specifically, relates to a wound therapy system including a portable container having a hydrophobic membrane configured to maximize fluid capacity of the container.

2. Background of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure therapy also known as suction or vacuum therapy has been used in treating and healing wounds. Application of negative pressure, e.g. reduced or subatmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound to be covered to facilitate suction at the wound area. A conduit is introduced through the wound covering to provide fluid communication to an external vacuum source. Atmospheric gas, wound exudates, or other fluids thus may be drawn from the reservoir through the fluid conduit to stimulate healing of the wound. Exudates drawn from the reservoir may be deposited in a collection canister or container.

SUMMARY

The present disclosure is directed to further improvements in negative or subatmospheric pressure therapy. In one embodiment, a subatmospheric pressure therapy system includes self-contained collection canister defining a cavity or chamber for receiving fluid, a vacuum source, and a power source. The vacuum source and fluid receiving cavity may be separated by a hydrophobic filter or membrane. The hydrophobic membrane prevents the aspiration of fluid into the vacuum source. The collection canister of the present disclosure may be placed on its side, tilted or possibly even inverted without affecting operation of the system. This is in contrast to current non-ambulatory fluid collection systems incorporating fluid receptacles which must be in a standing or upright position during operation. In such systems, once a sufficient volume of fluid has been collected in the canister, tipping or tilting of the canister causes the fluid in the canister to cover the hydrophobic membrane. When the hydrophobic membrane is covered by fluid, air is prevented from passing through the membrane, thereby blocking the suction provided by the vacuum source. Without suction, the wound therapy system is ineffective at drawing fluid from the wound. The problem of the hydrophobic membrane becoming covered by fluids may be further exaggerated in portable units which may be worn or carried by the subject.

In one embodiment, a portable system for subatmospheric pressure therapy in connection with healing a surgical wound includes a wound dressing dimensioned for positioning relative to a wound bed of a subject and a collection canister in fluid communication with the wound dressing. The canister includes a first vacuum chamber for drawing a vacuum and a second fluid chamber for collecting fluids removed from the wound dressing under the vacuum. The vacuum chamber may have a vacuum and a power source. The canister further includes a hydrophobic membrane separating the first fluid chamber and the second vacuum chamber. The hydrophobic membrane is dimensioned to span a major portion of the cross-sectional area of the canister. The hydrophobic membrane may be dimensioned to substantially span an internal dimension of the collection canister.

The hydrophobic membrane may include one or more outwardly extending lobes. One of the benefits of these outwardly extending lobes is they may allow for flow in different system attitudes while maintaining the structural integrity of the system. The outwardly extending lobes may be arranged in staggered or symmetrical relation. The hydrophobic membrane may be releasably mountable to the canister, and, may be supported within a divider separating the first vacuum chamber and the second fluid chamber. The divider may include reinforcing ribs for structural support, especially in the areas between the lobes. The divider may constitute a screen or a mesh in the area beneath the hydrophobic membrane to provide additional mechanical support to the membrane. The hydrophobic membrane may be substantially Z-shaped.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 3B-3C are cross-sectional views illustrating the collection canisters of

FIGS. 2A-3A positioned on respective sides of the canister;

DETAILED DESCRIPTION

The hydrophobic membranes of the disclosure will be discussed in connection with use in a wound therapy system applying subatmospheric pressure for promoting healing of a wound. Although the membranes will be described as relates to a wound therapy system, alternative uses for the membranes are envisioned. The wound therapy system includes a wound dressing and a portable subatmospheric pressure mechanism in fluid communication with the wound dressing. The subatmospheric pressure mechanism applies subatmospheric pressure to the wound to effectively remove wound fluids or exudates captured by the composite wound dressing, and to increase blood flow to the wound bed, thereby enhancing cellular stimulation of epithelial and subcutaneous tissue. The wound therapy system may be entirely portable, i.e., it may be worn or carried by the subject such that the subject may be completely ambulatory during the therapy period. The wound therapy system may be entirely disposable after a predetermined period of use or may be individually disposable whereby some of the components are reused for a subsequent therapy application.

Figure 1:
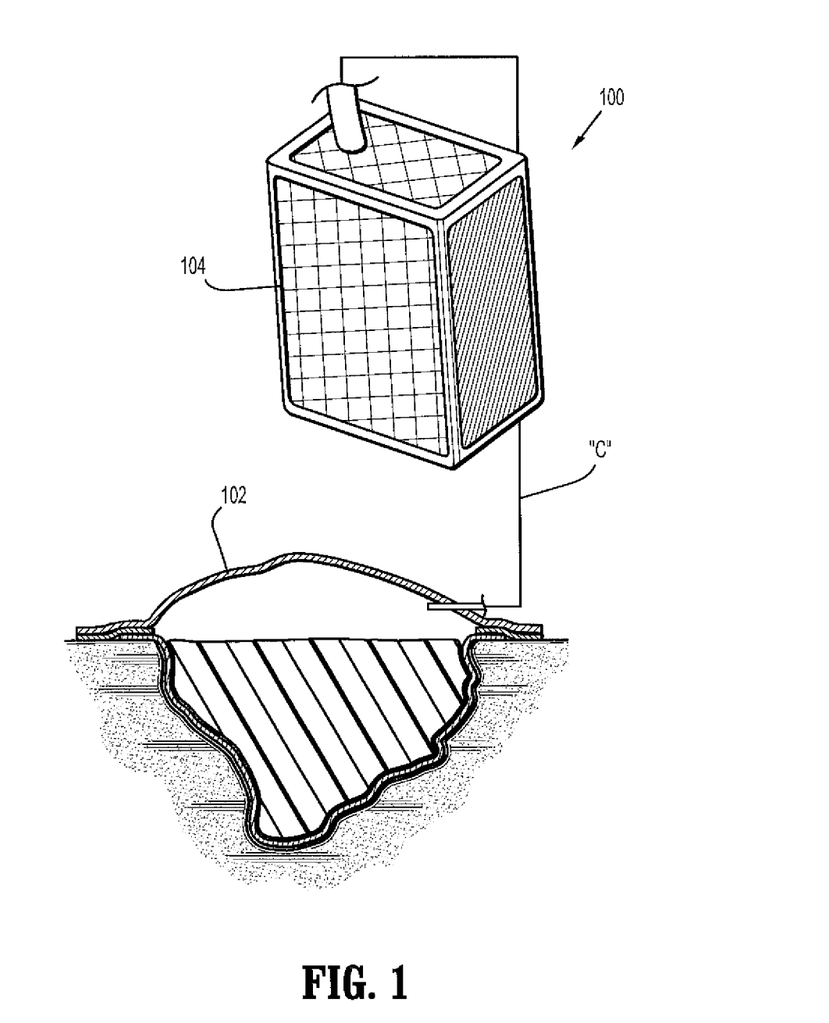
FIG. 1 is a perspective view of a portable wound therapy system.

Referring initially to FIG. 1, wound therapy system 100 is illustrated. Wound therapy system 100 includes composite wound dressing 102 and subatmospheric pressure mechanism or collection canister 104 in fluid communication with the wound dressing 102 through a conduit, identified schematically as reference character "c". For a more detailed description of wound dressing 102, including the composition and operation thereof, please refer to commonly assigned U.S. patent application Ser. No. 11/825,480, filed Jul. 6, 2007, the contents of which are incorporated herein by reference in their entirety.

Figure 2A:
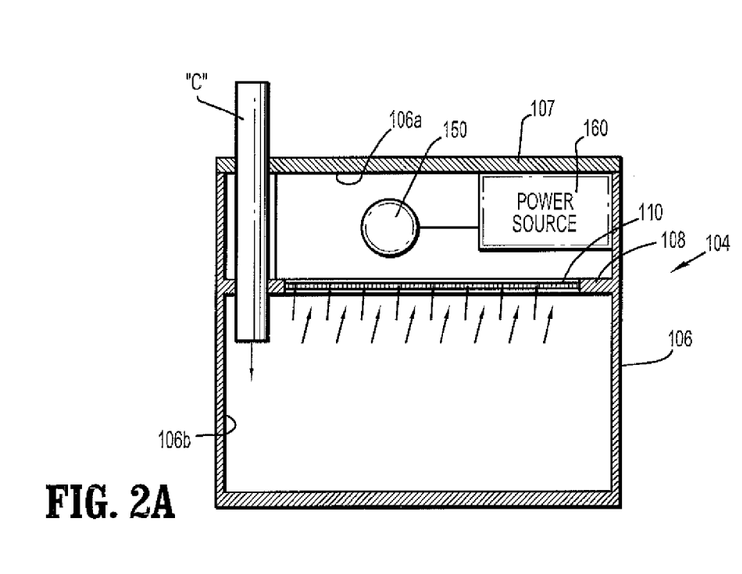
FIG. 2A is a cross-section said view of the collection canister of the portable wound therapy system of FIG. 1.
Figure 2B:
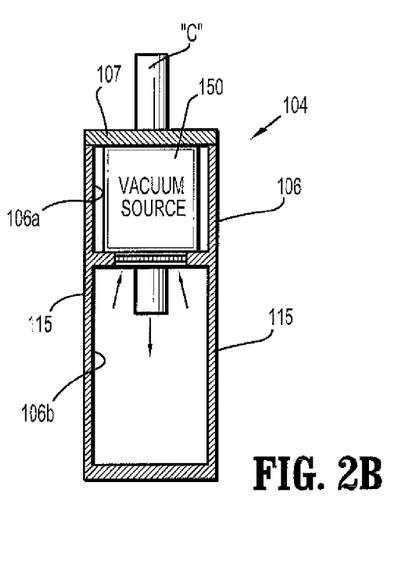
FIG. 2B is a cross-sectional end view of the collection canister of FIG. 2A.
Figure 2C:
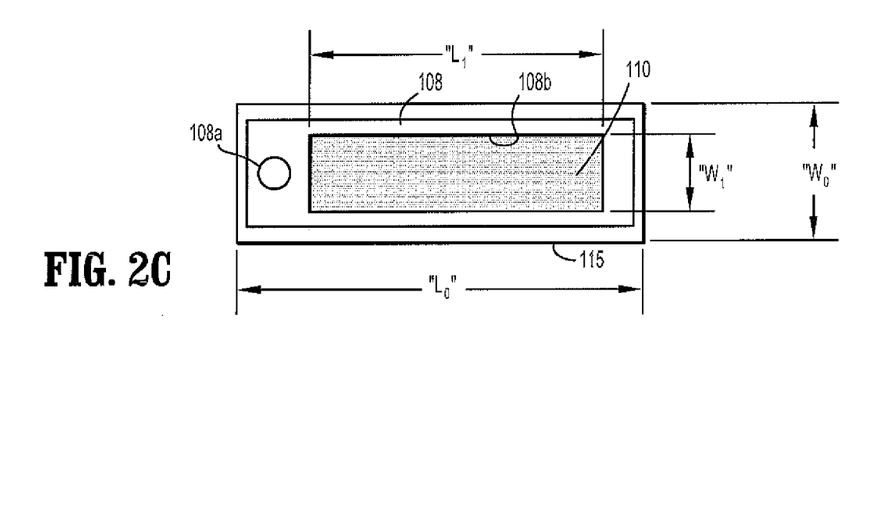
FIG. 2C is a top view of the collection canister of FIGS. 2A and 2B with the cover removed.

With reference now to FIGS. 2A-2C, the structure and operation of collection canister 104 will be described as it relates to the wound therapy system 100. Canister 104 includes housing 106 defining first chamber 106a and second chamber 106b. Housing 106 may be rigid, or, in the alternative, comprise a flexible material. First chamber 106a includes vacuum source 150 and power source 160. Vacuum source 150 may be any suitable vacuum pump adapted to present negative pressure either continuously or intermittently within wound dressing 102. Vacuum source 150 may be associated with computer logic, software or processing means to control operation of therapy system 100.

Second chamber 106b of canister 104 defines a fluid receiving cavity for receiving exudates and/or fluid "F" from wound dressing 102 (FIG. 1). First and second chambers 106a, 106b are separated by divider 108. Divider 108 includes hydrophobic membrane 110 adapted to prevent aspiration of fluid "F" collected in second chamber 106b into vacuum source 150. Container 104 further includes cover 107 positioned to seal second chamber 106a. Conduit "c" extends through cover 107 and divider 108 and terminates adjacent an upper area or section of canister 104.

With continued reference to FIGS. 2A-2C, divider 108 includes opening 108a for receiving conduit "c" therethrough, and rectangular opening 108b for at least partially receiving hydrophobic membrane 110. Although a rectangular opening 108b is depicted, other shapes for hydrophobic membrane 110 and opening 108b are envisioned. Opening 108a may define the outlet of vacuum source 150 which draws a vacuum within second chamber 106b. Although the rectangular opening is 108b implies a hole or void, this opening may consist of a screen, mesh, or grill to provide structural support to the hydrophobic membrane 110 while still allowing air flow through the membrane.

Figure 3A:
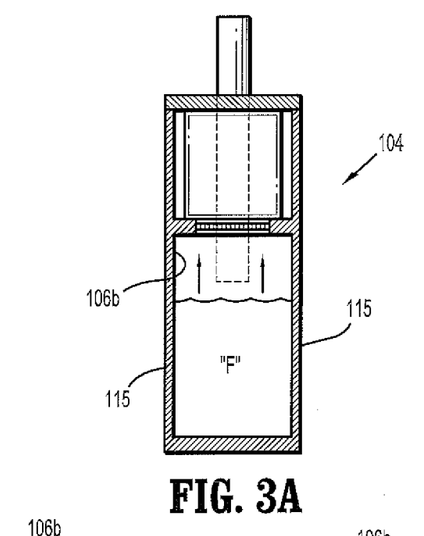
FIG. 3A is a cross-sectional view of the collection canister of FIGS. 2A-2C, in an upright position.
Figure 3B:
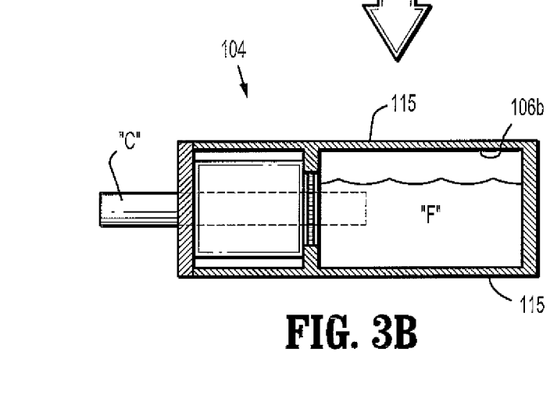
Figure 3C:
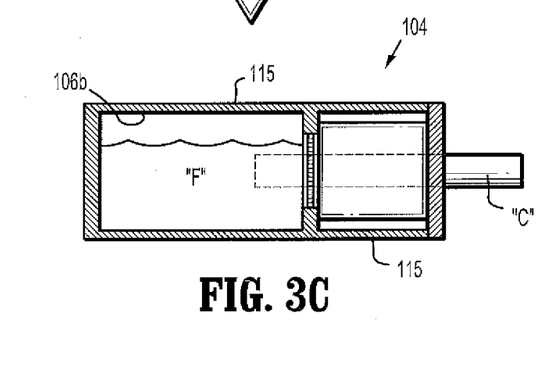

Hydrophobic membrane 110 spans a substantially large surface area or cross-section of canister 104 relative to conventional filters which typically cover a small opening adjacent the vacuum pump. Accordingly, as depicted in FIGS. 3B-3C, when canister 104 is tilted or placed on one of its sides 115, unless the canister 104 is substantially full with fluids "F" or exudates, at least a portion of hydrophobic membrane 110 will remain free of fluid thereby permitting continued vacuum draw through hydrophobic membrane 110, divider 108 and within canister 104. Thus, the relatively large surface area of hydrophobic membrane 110 enables continued use of system 100 even when canister 104 is positioned on its side 115 or tilted. In one aspect, hydrophobic membrane 110 encompasses at least seventy-five (75%) percent of the cross-section of canister 104 and has a length and width closely approximating the respective length and width of "$L_1, W_1$". In one embodiment, hydrophobic membrane 110 defines a length "$L_1$" and a width "$W_1$" ranging from about 65%-90% the respective length "$L_0$" and width "$W_0$" of canister 104.

Once hydrophobic membrane 110 is completely covered by fluid "F", in the event second chamber 106b is near capacity and canister 104 is placed on either side 115, or when second chamber 106b is completely full, vacuum source 150 may no longer draw air through hydrophobic membrane 110. Once air can no longer be drawn through hydrophobic membrane 110, the suction drawing fluid "F" from wound dressing 102 is ceased and fluids "F" are no longer drawn into second chamber 106b. Canister 104 then may be emptied or replaced, and therapy may be continued.

Figure 4:
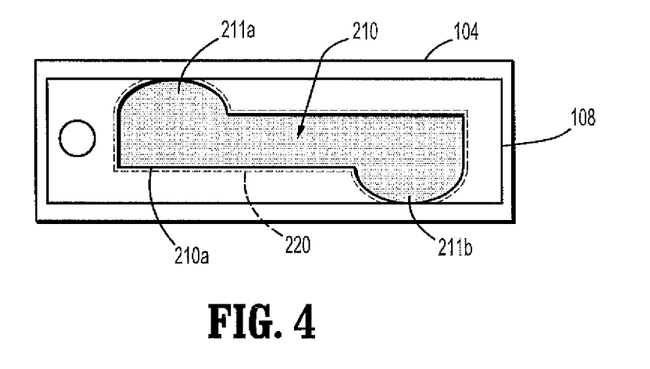
FIG. 4 is top view of a collection canister including an alternate embodiment of a hydrophobic membrane in accordance with an aspect of the present disclosure.
Figure 5:
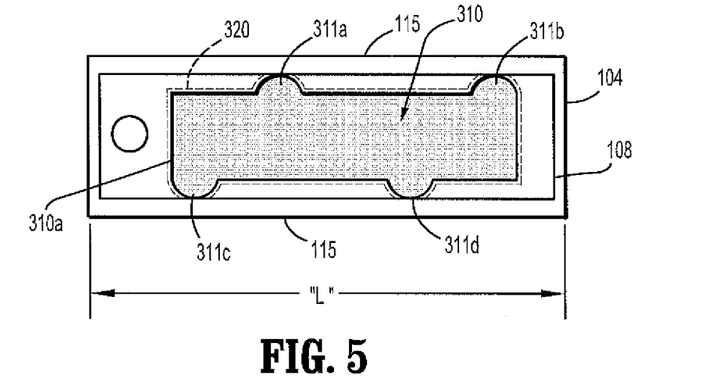
FIG. 5 is top view of a collection canister including another alternate embodiment of a hydrophobic membrane in accordance with an aspect of the present disclosure.
Figure 6:
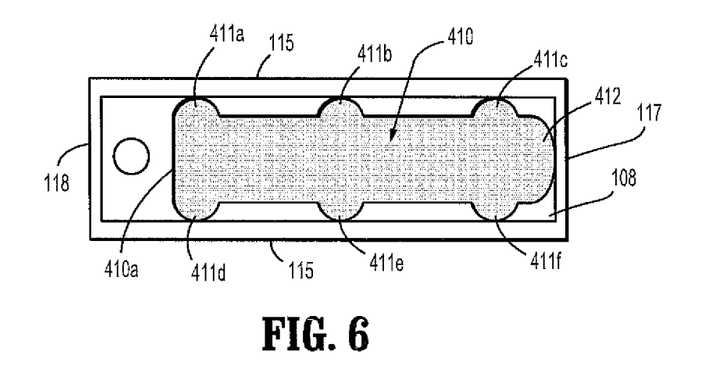
FIG. 6 is top view of a collection canister including another embodiment of a hydrophobic membrane in accordance with an aspect of the present disclosure.

With reference now to FIGS. 4-6, other embodiments of collection canisters including hydrophobic membranes according to the present disclosure will now be described and are shown generally as hydrophobic membranes 210, 310, 410. Each of hydrophobic membranes 210, 310, 410 is configured to maximize the effective working area of the membrane to maintain the vacuum draw during manipulation or transfer of the ambulatory system. Each of hydrophobic membranes 210, 310, 410 is securely received within, or mounted to, divider 108.

Referring initially to FIG. 4, hydrophobic membrane 210 defines a substantially rectangular body 210a including opposing first and second lobes 211a, 211b extending outwardly along a length thereof. For example, hydrophobic membrane 210 may define a substantially Z-shaped member. Divider 108 may have a corresponding inner wall defining a complementary Z-shaped opening 220 (shown in phantom) for at least partially accommodating hydrophobic membrane 210. Opening 220 follows the contour of the periphery of hydrophobic membrane 210. Although the opening 220 implies a hole or void, this opening may consist of a screen, mesh, or grill to provide structural support to the hydrophobic membrane 210 while still allowing air flow through the membrane 210.

Hydrophobic membrane 210 is adapted to permit air flow when canister 104 is in an upright position, tilted position or on either side 115. In particular, the positioning of lobes 211a, 211b in opposed relation both vertically and horizontally with respect to FIG. 4 increases the possibility that one of the lobes 211a, 211b will be free of, or not covered by, liquid when canister 104 is tilted or placed on its side thereby permitting continued vacuum draw within canister 104. Lobes 211a, 211b may be dimensioned to extend substantially to side wall 115 of canister 104 to maximize the effective operating area of hydrophobic membrane 210.

Referring now to FIG. 5, this embodiment of hydrophobic membrane 310 includes a body 310a having multiple outwardly extending lobes 311a, 311b, 311c, 311d staggered along the length "L". Hydrophobic membrane 310 may include any number of lobes 311a, 311b, 311c, 311d. As with lobes 211a, 211b, lobes 311a, 311b, 311c, 311d permit air to flow through hydrophobic membrane 310 when canister 104 is in an upright or tilted position. The additional lobes 311a, 311b, 311c, 311d along the length of rectangular body 310a may enhance vacuum flow through hydrophobic membrane 310. Divider 108 may include a correspondingly shaped opening 320 (shown in phantom) for receiving membrane 310. It is envisioned that divider 108 may include ribbing or other structural support between lobes 311a, 311b, 311c, 311b to reinforce hydrophobic membrane 310 and/or to add structural integrity to canister 104.

With reference now to FIG. 6, another embodiment of hydrophobic membrane 410 is illustrated. Hydrophobic membrane 410 includes a body 410a having multiple opposing lobes 411a, 411b, 411c, 411d extending outwardly along a length thereof. Hydrophobic membrane 410 further includes lobe 412 which extends to end wall 117 of canister 104. As with hydrophobic membranes 210, 310, lobes 411a, 411b, 411c, 411d permit air to flow through hydrophobic membrane 410 when canister 104 is in an upright position, tilted position or positioned on one of its sides 115. In addition, lobe 412 further permits air to flow through hydrophobic membrane 410 if canister 104 is positioned on opposed end wall 118. In particular, when canister 104 is positioned on end wall 118, a volume of air will be present adjacent end wall 117 (provided canister 104 is not full with fluids "F") to permit continued vacuum draw through lobe 412 and into second chamber 106b of canister 104.

Figure 7:
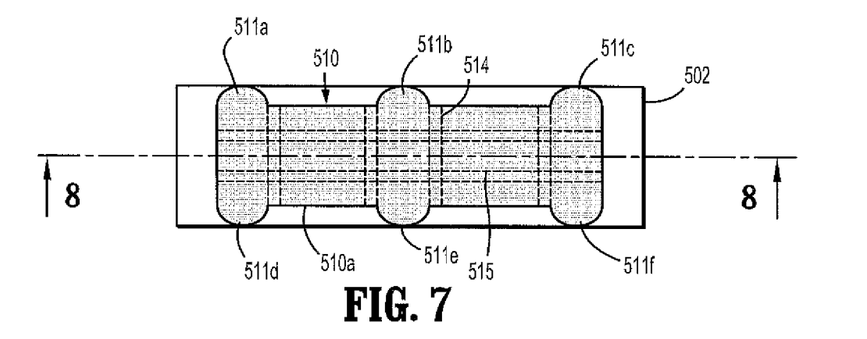
FIG. 7 is top view of another embodiment of a hydrophobic membrane in accordance with an aspect of the present disclosure.
Figure 8:
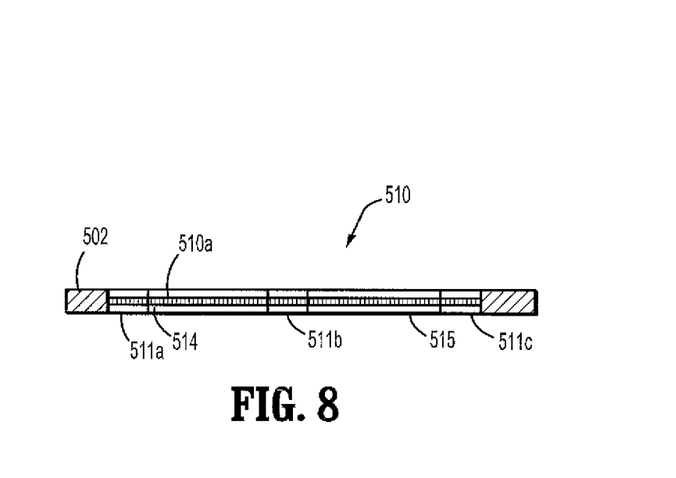
FIG. 8 is a cross-sectional side view of the hydrophobic membrane of FIG. 7.

Referring now to FIGS. 7 and 8, another alternate embodiment of according to the present disclosure is illustrated. Filter assembly 510 is independent of canister 104 (FIG. 1) and may be releasably mounted within canister 104 by conventional means. Filter assembly 510 may be disposed after use if desired and replaced with a new filter assembly 510 which may be mounted within canister 104. Filter assembly 510 includes base 502 and filter element 512 within the base 502. Base 502 defines a substantially planar member configured to be received in a fluid collection canister (not shown). Base 502 may be adapted for selective attachment with or permanently fixed to the collection canister 104. Filter membrane 512 defines a substantially rectangular area and possesses multiple opposing lobes 511a, 511b, 511c, 511d, 511e, 511f extending outwardly along a length thereof. Additional lobes 516 (shown in phantom) may be provided adjacent the end of filter membrane 512. Base 502 may further include lateral and longitudinal supports 514, 515 extending across the width and length of hydrophobic membrane 510, respectively. Filter membrane 512 functions in a similar manner to the filter membranes described in connection with the prior embodiments by increasing the overall effective operable area of the filter to permit vacuum draw in the event of tipping or inversion of canister 104.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A collection canister comprising:
   a first chamber fluidly connectable to a vacuum source for drawing a vacuum;
   a second chamber including a cavity for receiving fluid drawn under the vacuum;
   a hydrophobic membrane separating the first chamber and the second chamber, the hydrophobic membrane dimensioned to span at least a portion of the cross-sectional area of the collection canister and including one or more lobes extending outwardly relative to a central longitudinal axis extending along a length of the collection canister, the one or more lobes positioned and dimensioned for permitting vacuum draw upon tilting, inverting, or placing the collection canister on a side thereof; and
   a divider supporting the hydrophobic membrane between the first chamber and the second chamber, wherein the divider includes one of a screen, grill, or a mesh.

2. The collection canister according to claim 1, wherein the hydrophobic membrane is dimensioned to span an internal dimension of the collection canister.

3. The collection canister according to claim 1, wherein the hydrophobic membrane includes a plurality of lobes arranged in staggered relation with respect to the central longitudinal axis.

4. The collection canister according to claim 1, wherein the hydrophobic membrane includes a plurality of lobes arranged in symmetric relation with respect to the central longitudinal axis.

5. The collection canister according to claim 1, wherein the hydrophobic membrane is releasably mountable in the collection canister.

6. The collection canister according to claim 1, wherein the hydrophobic membrane includes a first lobe disposed outward of a first side of the central longitudinal axis and a second lobe disposed outward of a second side of the central longitudinal axis.

7. The collection canister according to claim 1, wherein the hydrophobic membrane includes at least two first lobes disposed outward of a first side of the central longitudinal axis and at least two second lobes disposed outward of a second side of the central longitudinal axis.

8. The collection canister according to claim 7, wherein the at least two first lobes are longitudinally spaced relative to each other along the central longitudinal axis.

9. The collection canister according to claim 7, wherein the at least two second lobes are longitudinally spaced relative to each other along the central longitudinal axis.

10. The collection canister according to claim 1, wherein the first chamber includes the vacuum source and a power source operably connected to the vacuum source.

11. A method comprising:
providing a collection canister including a first chamber containing a vacuum source and a second chamber defining a cavity for receiving fluids drawn by the vacuum source; and
mounting a hydrophobic membrane within a divider separating the first chamber and the second chamber, the hydrophobic membrane dimensioned to span an internal dimension of the collection canister and including one or more lobes extending outwardly relative to a central longitudinal axis extending along a length of the collection canister, the one or more lobes positioned and dimensioned for permitting vacuum draw upon tilting, inverting, or placing the collection canister on a side thereof.

12. The method according to claim 11, wherein mounting the hydrophobic membrane comprises releasably mounting the hydrophobic membrane in the collection canister.

13. The method according to claim 12, further comprising sealing the collection canister.

14. The method according to claim 13, wherein sealing the collection canister comprises positioning a cover adjacent an upper area of the first chamber of the collection canister.

15. The method according to claim 14, further comprising extending a conduit from the second chamber, through the first chamber, and the cover.

16. A collection canister comprising:
a first chamber fluidly connectable to a vacuum source for drawing a vacuum;
a second chamber including a cavity for receiving fluid drawn under the vacuum;
a hydrophobic membrane separating the first chamber and the second chamber, the hydrophobic membrane dimensioned to span at least a portion of the cross-sectional area of the collection canister and including one or more lobes extending outwardly relative to a central longitudinal axis extending along a length of the collection canister, the one or more lobes positioned and dimensioned for permitting vacuum draw upon tilting, inverting, or placing the collection canister on a side thereof; and
a divider supporting the hydrophobic membrane between the first chamber and the second chamber, wherein the divider includes reinforcing ribs.

* * * * *